United States Patent [19]

Chinn

[11] 4,388,311

[45] Jun. 14, 1983

[54] METHOD FOR THE INDUCTION OF MENSES

[75] Inventor: Leland J. Chinn, Morton Grove, Ill.

[73] Assignee: G. D. Searle & Co., Skokie, Ill.

[21] Appl. No.: 375,619

[22] Filed: May 6, 1982

[51] Int. Cl.³ .............................................. A61K 31/56
[52] U.S. Cl. .................................... 424/238; 424/241
[58] Field of Search ....................... 424/241, 243, 238

[56] References Cited

U.S. PATENT DOCUMENTS 3,296,255  1/1967  Clinton et al. ............. 260/239.55 R Primary Examiner—Elbert L. Roberts
Attorney, Agent, or Firm—James G. Passe

[57] ABSTRACT

The invention relates to a method for the induction of menses or the termination of pregnancy by administration of a compound of Formula IV.

6 Claims, No Drawings

METHOD FOR THE INDUCTION OF MENSES

BACKGROUND OF THE INVENTION

The present invention relates to certain novel methods using known pharmacological agents. In particular the invention relates to compounds of the formula:

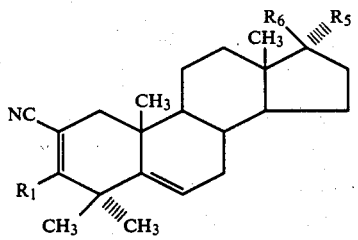

useful for the induction of menses and the termination of pregnancy in mammals. The compounds show increased activity when compared to prior art compounds.

Compounds which show activity for induction of menses and termination of pregnancy are well known. Estrogens have been used widely for induction of menses in the menopausal female (see e.g. U.S. Pat. No. 4,154,820). Progesterone and its derivatives have been shown to be useful for primary and secondary amenorrhea as described by Wiechert in U.S. Pat. No. 3,812,166.

PRIOR ART

Various steroids are known in the art for control of menses and induction of pregnancy as indicated above. In addition, U.S. Pat. No. 3,246,255 describes a 2-cyanosteroid that shows activity as pituitary inhibitors, electrolyte modifying agents, and hypotensive coronary dilators. U.S. Pat. No. 4,160,027 describes certain 2-cyano-4,5-epoxy steroids useful as interceptive agents. The 3-oxo compounds of the invention are described generically in U.S. Pat. No. 3,296,255 to Sterling. The Sterling patent describes the activity of the compounds of Formula IV as adrenal and pituitary inhibitors, electrolyte modifying agents and as hypotensive and coronary dilating agents. The Sterling patent also describes methods of making compounds of the instant invention.

SUMMARY OF THE INVENTION

The invention particularly provides a method for the induction of menses or the termination of pregnancy which comprises administering an amount of a compound of Formula IV.
wherein $R_1$ is:
(a) hydroxy;
(b) $R_2COO-$;
(c) $HOOC-R_3-COO-$; or
(d) $R_4C(=O)-R_3-COO-$;
wherein $R_2$ is:
(a) alkyl of from 1 to 10 carbon atoms, inclusive;
(b) oxacycloalkyl of from 4 to 7 carbon atoms and one ring oxygen atom;
(c) cycloalkyl of from 5 to 10 carbon atoms, inclusive;
(d) ring-unsaturated oxacycloalkyl of from 4 to 7 carbon atoms and one ring oxygen atom; or
(e) ring-unsaturated cycloalkyl of from 5 to 10 carbon atoms, inclusive;
wherein $R_3$ is:
(a) alkylene of from 1 to 10 carbon atoms, inclusive; or
(b) cycloalkylene of from 5 to 10 carbon atoms, inclusive;
wherein $R_4$ is:
(a) alkyl of from 1 to 6 carbon atoms, inclusive;
wherein $R_5$ is:
(a) hydrogen; or
(b) alkyl of from 1 to 6 carbon atoms, inclusive;
wherein $R_6$ is:
(a) hydroxy; or
(b) $-C(=O)-CH_3$.

Examples of alkyl of from 1 to 10 carbon atoms, inclusive are methyl, ethyl, propyl, butyl, pentyl, hexyl, heptyl, octyl, nonyl, decyl and the branched and side chain isomers thereof.

Examples of oxacycloalkyl of from 4 to 7 carbon atoms and one ring oxygen atom are oxacyclopentyl, oxacycloheptyl, oxacyclohexyl and oxacyclooctyl.

Examples of cycloalkyl of from 5 to 10 carbon atoms, inclusive are cyclopentyl, cyclohexyl, cycloheptyl, cyclooctyl, cyclononyl and cyclodecyl.

Examples of ring-unsaturated oxacycloalkyl of from 4 to 7 carbon atoms and one ring oxygen atom are oxacyclopentenyl, oxacyclohexenyl, oxacycloheptenyl, oxacyclooctenyl, furanyl (oxacyclopentadienyl), pyranyl (oxacyclohexadienyl), oxacycloheptodienyl, and oxacyclooctadienyl.

Examples of ring-unsaturated cycloalkyl of from 5 to 10 carbon atoms, inclusive, are cyclopentenyl, cyclohexenyl, etc., cyclopentodienyl, cyclohexadienyl, etc. Examples of cycloalkylene of from 5 to 10 carbon atoms, inclusive are cyclohexylene, cycloheptylene, cyclooctylene, cyclononylene and cyclodecylene.

Successful implantation and the maintenance of the initial stages of pregnancy in humans are dependent upon the availability of adequate amounts of ovarian protesterone. An important step in the biosynthetic pathway for progesterone is the conversion of pregnenolone to progesterone. This reaction is catalyzed by the $3\beta$-hydroxysteroid dehydrogenase/$\Delta^{5-4}$, 3-ketoisomerase ($\Delta^5$,$3\Delta$-HSD) enzyme system. Several known inhibitors of this enzyme system have already been shown to inhibit selectively or predominantly either gonadal/placental production of progesterone (see Creange et al., Fertility and Sterility 30: pps 86–90, 1978) or the adrenal production of progesterone (see Potts et al., Steroids 32: pps 257–267, 1978). An in vitro technique for measuring the amount of progesterone produced by luteal microsomes incubated at 37° C. with pregnenolone as substrate and NAD as cofactor has been developed. The progesterone produced can be measured spectrophotometrically in the ultraviolet range at 240 nm. Drugs which inhibit biosynthesis of progesterone would be useful as contraceptive and contragestational agents.

A. Incubation

Luteal tissue is collected from immature pseudopregnant rats on day three or four and homogenized at 8 milligrams per milliliter in 0.25 M sucrose in Kreb's Ringer bicarbonate solution without calcium (pH 7.4) and centrifuged at 750×g for ten minutes to remove nuclei and cell debris. The supernatant is then centrifuged at 7,000×g for twelve minutes to remove the mitochondria, leaving only the microsome-cytosol in the supernatant. Pregnenolone is used as substrate in a concentration of 157.2 μM and 4.04 micromoles (6 milligrams/0.5 ml) of NAD is used as cofactor. The order of addition of components of the incubate is 0.1 ml pregnenolone solution (100 micrograms/0.1 ml ethanol), 0.5 ml buffer, 0.02 ml ethanol (control mixture) or the inhibitor in 0.02 ml ethanol (test mixture), 1 ml microsome-cytosol and 0.5 ml NAD solution, thus making up a total volume of 2.12 ml. The reaction is initiated by the addition of the cofactor. The incubation is carried out for one hour at 37° C. At the end of one hour incubation samples are immersed in a Dry Ice ethanol bath to stop the reaction. Samples are stored at minus 20° C. until extraction for progesterone with petroleum ether.

B. Extraction

Incubates are thawed in a warm water bath at 50° C. and extracted twice with petroleum ether. The extract is dried under an air manifold and reconstituted in 2 ml of absolute ethanol. The progesterone concentration of the reconstitute is determined in a standard size quartz cuvette in a Gilford 240 spectrophotometer at 240 nm (uv). A standard progesterone curve is prepared using progesterone diluted in absolute ethanol in doses of 1, 2, 4, 8, 12, 16, 20, 40, 60, 80 and 100 micrograms/0.1 ml. These doses were added to 2.0 ml of deionized distilled water and extracted along with the samples from each incubation.

By virtue of the above described activity the compounds of Formula IV are useful in inducing menses and for the termination of pregnancy. A physician of ordinary skill can readily determine a subject who is in need of such treatment. Regardless of the route of administration selected, compounds of the present invention can be formulated into pharmaceutically acceptable dosage forms by conventional methods known to the pharmaceutical art.

The compounds can be administered in such oral unit dosage forms as tablets, capsules, pills, powders or granules. They also may be administered rectally or vaginally in such forms as suppositories or bougies. They also may be introduced in the form of eyedrops, intraparentally, subcutaneously or intramuscularly, using forms known to the pharmaceutical art. In general, the preferred form of administration is oral.

An effective but non-toxic quantity of the compound is employed in treatment. The dosage regimen of the compounds of this invention is selected in accordance with a variety of factors including the type, age, weight and medical condition of the mammal, the route of administration and the particular compound employed. An ordinary skilled physician or veterinarian will readily determine and prescribe the effective amount of the compound of the instant invention.

Dosages of the compound of the invention are ordinarily in the area of 1 milligram per kilogram up to at most 20 milligrams per kilogram orally. When the other forms of administration are employed equivalent doses are administered.

DESCRIPTION OF THE PREFERRED EMBODIMENTS

The compounds of the instant invention may among other methods be prepared according to the scheme in U.S. Pat. No. 3,296,255, using appropriate starting materials as can be deduced by one skilled in the art. Following are examples of the manufacture of each compound. One skilled in the art will readily deduce other methods for making the compounds.

EXAMPLE 1

Preparation of 3-(acetyloxy)-17β-hydroxy-4,4,17α-trimethylandrosta-2,5-diene-2-carbonitrile.

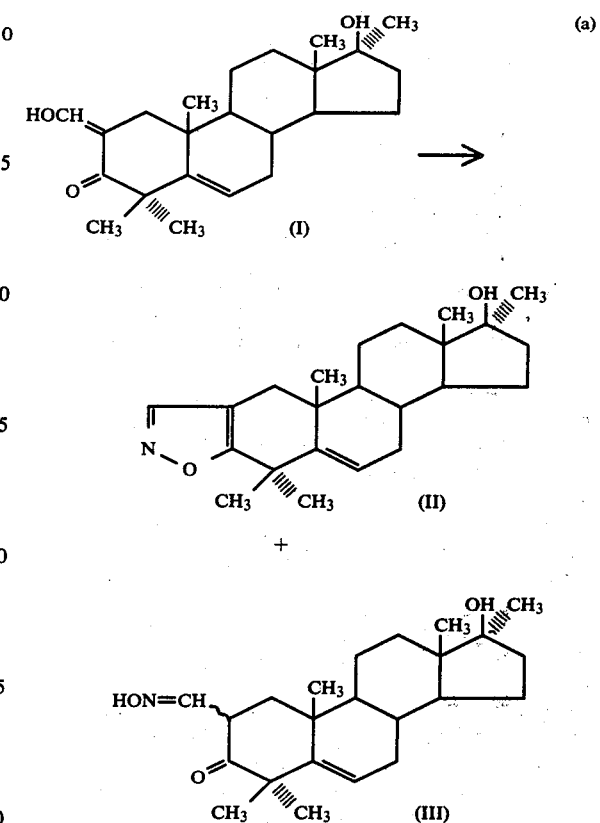

A mixture of 12 g of (I), 250 ml of 95% ethanol, 2.8 g of hydroxylamine hydrochloride, and 2.8 g of sodium acetate was stirred and heated under reflux for 2 hr. Then 1.0 g of pyridine hydrochloride was added to the mixture, which contained the oxime (III) as well as the isoxazole (II). The mixture was stirred and heated under reflux for an additional 20 minutes, after which approximately 100 ml of solvent was removed by distillation under reduced pressure. The residue was poured into 2 liters of ice water. After ca. 1 hr. the solid, II, was collected by filtration, washed with water, and dried.

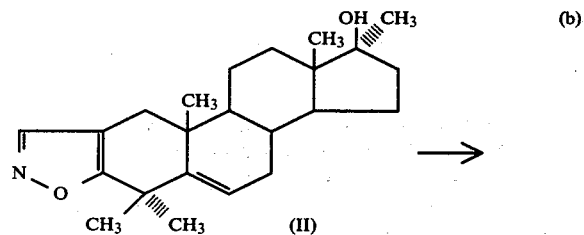

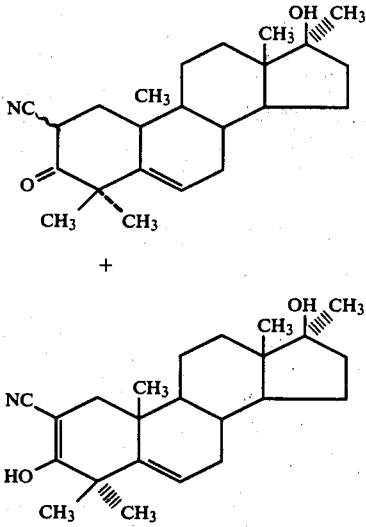

+

To a solution of 10 g of (II) in 80 ml of tetrahydrofuran was added 3.5 g of sodium methoxide. The reaction mixture was stirred at 25° C. for 1 hr. after which it was diluted with 1 liter of water. The resultant mixture was extracted with ether, and the ether extract was set aside. The aqueous solution was acidified with 6 N HCl. The solid which formed was collected by filtration, washed with water, and dried. Crystallization from ethyl acetate gave a product melting at 224°–226° C. NMR indicated it was a mixture of 2α-cyano-17β-hydroxy-4,4,17α-trimethylandrost-5-en-3-one, 2β-cyano-17β-hydroxy-4,4,17α-trimethylandrost-5-en-3-one, and 2-cyano-4,4,17α-trimethylandrosta-2,5-diene-3,17β-diol.

(c)

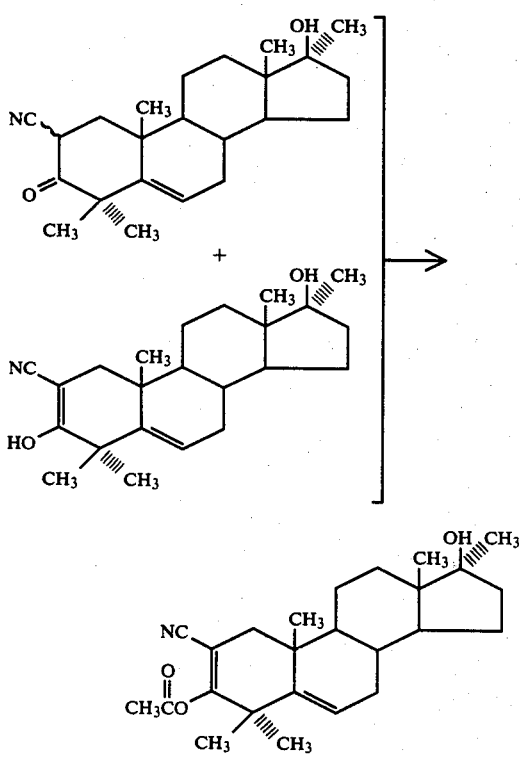

A mixture of 5.0 g of 2α-cyano-17β-hydroxy-4,4,17α-trimethylandrost-5-en-3-one, 2β-cyano-17β-hydroxy-4,4,17α-trimethylandrost-5-en-3-one, and 2-cyano-4,4,17β-trimethylandrosta-2,5-diene-3,17β-diol was dissolved in 40 ml of pyridine. After the addition of 30 ml of acetic anhydride, the reaction mixture was allowed to stand at 25° C. for 18 hr. The mixture was then diluted with a large volume (ca. 1 liter) of ice water. The mixture was allowed to stand for 0.5 hr. after which the solid product was collected by filtration, washed with water, and dried. Crystallization from ether-hexane afforded 4.5 g of the title compound, (IV), mp 159°–161°. Concentration of the mother liquor gave additional quantity of the title compound, mp 158°–161°.

EXAMPLE 2

Preparation of 2-cyano-4,4,17α-trimethylandrosta-2,5-diene-3,17β-diol 3,17β-diacetate.

A mixture of 1.5 g of 2α-cyano-17β-hydroxy-4,4,17α-trimethylandrost-5-en-3-one, 2β-cyano-17β-hydroxy-4,4,17α-trimethylandrost-5-en-3-one, and 2-cyano-4,4,17α-trimethylandrosta-2,5-diene-3,17β-diol was dissolved in 100 ml of isopropenyl acetate. After 160 mg of p-toluensulfonic acid monohydrate was added, the reaction mixture was stirred and heated uner reflux in a nitrogen atmosphere for 17 hours. Then the reaction mixture was concentrated by slow distillation over a period of 5 hours. The residue was cooled in an ice bath and diluted with a 1% solution of aqueous sodium bicarbonate. The resultant mixture was extracted with ether. The ether extract was washed first with water and then with saturated sodium chloride, dried over anhydrous sodium sulfate, and distilled to dryness under reduced pressure. Chromatography of the residue gave a crystalline product which was crystallized from ether to afford the title compound, mp 171°–174°.

EXAMPLE 3

Preparation of 3-(trimethylacetyloxy)-17β-hydroxy-4,4,17α-trimethylandrosta-2,5-diene-2-carbonitrile.

To a solution of 330 mg. of a mixture of 2α-cyano-17β-hydroxy-4,4,17α-trimethylandrost-5-en-3-one, its 2β-cyano isomer, and 2-cyano-4,4,17α-trimethylandrosta-2,5-diene-3,17β-diol in 4.0 ml of pyridine was added 3.0 ml of trimethylacetyl chloride. The reaction mixture was stirred at 25° C. for 3 hrs. Then it was diluted with water whereupon it became warmed. After the mixture had cooled to 25° C., it was extracted with ether. The ether extract was washed successively with water, cold 10% hydrochloric acid, and 5% sodium bicarbonate solution, dried over anhydrous sodium sulfate, and evaporated to dryness. The residue was chromatographed on silica gel to afford the product, mp at 178°–180° after crystallization from a mixture of ethyl acetate and hexane.

EXAMPLE 4

Preparation of 3-[3-(methoxycarbonyl)propanoyloxy]-17β-hydroxy-4,4,17α-trimethylandrosta-2,5-diene-2-carbonitrile.

Following the procedure employed in Example 3, the mixture of 2α-cyano-17β-hydroxy-4,4,17α-trimethylandrost-5-en-3-one, its 2β-cyano isomer and 2-cyano-4,4,17α-trimethylandrosta-2,5-diene-3,17β-diol was acylated with the half acid chloride half ester of succinic acid in pyridine to afford the enol succinate methyl ester title compound, mp 124°–125° after crystallization from ether-hexane.

EXAMPLE 5

Preparation of 3-(2-furoyloxy)-17β-hydroxy-4,4,17α-trimethylandrosta-2,5-diene-2-carbonitrile.

Following the procedure employed in Example 3, the mixture of 2α-cyano-17β-hydroxy-4,4,17β-trimethylandrost-5-en-3-one, its 2β-cyano isomer and 2-cyano-4,4,17β-trimethylandrosta-2,5-diene-3,17β-diol was acylated with 2-furoyl chloride in pyridine to afford the enol furoate chloride title compound mp 187°–191° after crystallization from dichloromethane-hexane.

EXAMPLE 6

Preparation of 3-(acetyloxy)-4,4-dimethylpregna-2,5-diene-20-one-2-carbonitrile.

Following the procedure employed in the preparation of 3-(acetyloxy)-17β-hydroxy-4,4,17α-trimethylandrosta-2,5,diene-2-carbonitrile (Example 1), the mixture of 2α-cyano-4,4-dimethylpregn-5-en-3,20-dione, its 2β-cyano isomer, and 2-cyano-3-hydroxy-4,4-dimethylpregna-2,2-diene-20-one was acetylated with acetic anhydride in pyridine to afford the enol acetate, mp 190°–191° after crystallization from dichloromethane-hexane.

EXAMPLE 7

Preparation of 3-(α-furoyloxy)-4,4-dimethylpregna-2,5-dien-20-one-2-carbonitrile Following the procedure employed in the preparation in Example 5, the mixture of 2α-cyano-4,4-dimethylpregn-5-ene-3,20-dione, its 2β-cyano isomer and 2-cyano-3-hydroxy-4,4-dimethylpregna-2,5-dien-20-one was acylated with 2-furoyl chloride in pyridine to afford the corresponding enol furoate, mp 217°–218° after crystallization from dichloromethane-hexane.

EXAMPLE 8

The following tables list the results for a compound of Formula IV as compared with a control of previously known 2α-cyano-17β-hydroxy-3-oxo-4,4,17α-trimethylandrost-5-end (Cyanoketone) for termination of pregnancy.

TABLE 1

Comparison Between 3-(Acetyloxy)-17β-hydroxy-4,4,17-trimethylandrosta-2,5-diene-2-carbonitrile and Cyanoketone Administered Intragastrically for Four Days on Pregnancy Termination in Rats[1]

| Treatment | Dose (mg/kg/day) | Number of Rats Pregnant Number of Rats Treated | (Percent) | Fetal viability Normal Fetuses/ Implantation Sites | (Percent) | Serum Progesterone ng/ml + S.E. | (Percent of Control) | Adrenal Wt. mg + SE |
|---|---|---|---|---|---|---|---|---|
| 3-(Acetyloxy)- 17β-hydroxy- 4,4,17-trimethyl- androsta-2,5- diene-2- carbonitrile | 16 | 0/10 | (0) | 0/111$^a$ | (0)$^a$ | 13.4 + 2.0$^a$ | (29)$^a$ | 72.1 + 2.1$^b$ |
| | 8 | 0/10 | (0) | 0/95$^a$ | (0)$^a$ | 18.1 + 2.5$^a$ | (40)$^a$ | 70.3 + 3.1$^b$ |
| | 4 | 0/10 | (0) | 0/112$^a$ | (0)$^a$ | 13.4 + 3.9$^a$ | (29)$^a$ | 68.6 + 2.3$^b$ |
| | 2 | 7/9 | (78) | 60/89 | (67) | 49.6 + 6.2$^a$ | (109) | 68.9 + 2.2$^b$ |
| Control | — | 11/11 | (100) | 105/123 | (85) | 45.1 + 3.5$^a$ | (100) | 60.1 + 1.0 |
| Cyanoketone | 128 | 8/9 | (89) | 85/99 | (85) | 44.3 + 5.3 | (94) | 72.0 + 2.5 |
| | 64 | 2/11 | (18) | 24/128$^a$ | (19)$^a$ | 19.0 + 3.7$^b$ | (40)$^b$ | 83.5 + 4.8 |
| | 32 | 2/9 | (22) | 19/101$^a$ | (19)$^a$ | 31.5 + 6.7 | (67) | 66.4 + 3.3 |
| | 16 | 4/10 | (40) | 25/103$^a$ | (24)$^a$ | 41.4 + 7.1 | (88) | 74.5 + 3.1$^b$ |
| | 8 | 3/10 | (30) | 13/110$^a$ | (12)$^a$ | 30.2 + 3.8 | (64) | 65.7 + 2.5 |
| | 4 | ⅛ | (13) | 0/92$^a$ | (1)$^a$ | 35.5 + 6.2 | (75) | 75.0 + 3.5$^b$ |
| | 4 | ⅝ | (63) | 44/97$^b$ | (45)$^b$ | 33.8 + 3.8 | (72) | 76.9 + 3.7 |
| | 2 | 6/7 | (86) | 61/84 | (73) | 52.5 + 3.7 | (111) | 77.1 + 5.3 |
| | 1 | 5/5 | (100) | 49/54 | (91) | 47.3 + 3.5 | | 74.9 + 4.1 |
| Control | — | 10/10 | (100) | 111/119 | (93) | 49.1 + 4.5 | (100) | 65.7 + 2.7 |
| | — | 7/7 | (100) | 68/75 | (91) | 47.2 + 6.9 | (100) | 58.8 + 2.4 |
| | — | 6/6 | (100) | 47/50 | (94) | — | | 68.7 + 3.3 |
| Control[2] | — | 5/5 | (100) | 61/64 | (98) | 43.7 + 7.8 | (100) | 61.1 + 5.8 |

[1]Compounds were administered intragastrically once daily on days 10 through 13 of pregnancy in a vehicle consisting of PEG-400, propylene glycol and 100 percent ethanol (50:40:10, v:v:v). Serum for progesterone determination was drawn on day 11 of pregnancy, 24 hours after the initial injection of compound. The animals were autopsied on day 14 of pregnancy.
[2]Two control groups were tested in NB:2349-072. Progesterone levels on day 11 were determined in only the subcutanous corn-oil treated controls.
$^a$p < .01
$^b$p < .05 compared to appropriate control.

TABLE 2

Comparison Between 3-(Acetyloxy)-17β-hydroxy-4,4,17-trimethylandrosta-2,5-diene-2-carbonitrile and Cyanoketone Administered Subcutaneously on Termination of Pregnancy in Rats[1]

| Treatment | Dose (mg/kg/day) | Number of Rats Pregnant Number of Rats Treated | (Percent) | Fetal Viability Normal Fetuses/ Implantation Sites | (Percent) | Serum Progesterone ng/ml + S.E. | (Percent of Control) | Adrenal Wt. mg + SE |
|---|---|---|---|---|---|---|---|---|
| 3-(Acetyloxy)- 17β-hydroxy-4, 4,17-trimethyl- androsta-2,5- diene-2- | 16 | 0/8 | (0) | 0/98$^a$ | (0)$^a$ | 13.1 + 1.4$^a$ | (26)$^a$ | 93.8 + 4.9$^a$ |
| | 16 | 0/8 | (0) | 0/84$^a$ | (0)$^a$ | 15.7 + 2.8$^a$ | (36)$^a$ | 98.3 + 2.8$^a$ |
| | 8 | 0/9 | (0) | 0/112$^a$ | (0)$^a$ | 12.7 + 1.4$^a$ | (29)$^a$ | 83.9 + 2.0$^a$ |
| | 4 | 2/7 | (29) | 21/72$^a$ | (29)$^a$ | 14.2 + 4.9$^a$ | (32)$^a$ | 72.9 + 3.8$^b$ |

TABLE 2-continued

Comparison Between 3-(Acetyloxy)-17β-hydroxy-4,4,17-trimethylandrosta-2,5-diene-2-carbonitrile and Cyanoketone Administered Subcutaneously on Termination of Pregnancy in Rats[1]

| Treatment | Dose (mg/kg/day) | Number of Rats Pregnant Number of Rats Treated | (Percent) | Fetal Viability Normal Fetuses/ Implantation Sites | (Percent) | Serum Progesterone ng/ml + S.E. | (Percent of Control) | Adrenal Wt. mg + SE |
|---|---|---|---|---|---|---|---|---|
| carbonitrile | 2 | 9/9 | (100) | 101/109 | (93) | 52.3 + 2.8 | (91) | 81.2 + 3.2[a] |
| Control | — | 7/7 | (100) | 68/69 | (99) | 51.3 + 4.9[a] | (100) | 60.1 + 2.4 |
| Control | — | 6/6 | (100) | 61/67 | (91) | 43.9 + 2.0 | (100) | 58.4 + 2.2 |
| Control | — | 8/8 | (100) | 64/65 | (99) | 57.3 + 3.0 | (100) | 64.3 + 3.4 |
| Cyanoketone | 32 | 2/6 | (33) | 15/63[a] | (24)[a] | 35.1 + 7.8 | (70) | 94.8 + 8.9[a] |
|  | 16 | 3/9 | (33) | 26/103[a] | (25)[a] | 24.3 + 7.6[b] | (48)[b] | 77.0 + 4.5 |
|  | 16 | 2/8 | (25) | 11/94[a] | (12)[a] | 50.7 + 5.4 | (70)[2,b] | 105.2 + 6.7[a] |
|  | 8 | 5/10 | (50) | 36/119[a] | (30)[a] | 22.1 + 6.0[b] | (44)[b] | 78.8 + 3.9[b] |
|  | 4 | 3/6 | (50) | 27/87[a] | (32)[a] | 40.0 + 3.5 | (92) | 93.1 + 4.0[a] |
|  | 2 | 8/8 | (100) | 94/103[a] | (91)[a] | 40.8 + 2.2 | (94) | 91.6 + 4.6[a] |
|  | 1 | 7/7 | (100) | 80/82[b] | (98) | 54.1 + 2.6 | (124) | 83.4 + 4.0[b] |
| Control | — | 6/7 | (80) | 54/71 | (76) | 72.5 + 8.0[2] | (100)[2] | 67.0 + 3.8 |
| Control | — | 8/9 | (89) | 85/89 | (96) | 50.0 + 4.7 | (100) | 66.8 + 4.5 |
| Control | — | 5/5 | (100) | 61/64 | (98) | 43.3 + 7.8 | (100) | 61.1 + 5.8 |

[1]Compounds given subcutaneously in corn oil vehicle once daily on days 10 through 13 of pregnancy. Serum for progesterone determination was drawn on day 11 of pregnancy, 24 hours after the initial injection of compound. The animals were autopsied on day 14 of pregnancy.
[2]Serum progesterone values determined by RIA at Interlab Associates, Miami, Fl.
[a]p < .01;
[b]< .05 versus appropriate control.

TABLE 3

Comparison Between 3-(Acetyloxy)-17β-hydroxy-4,4,17-trimethylandrosta-2,5-diene-2-carbonitrile and Cyanoketone Administered Intragastrically on Day 10 of Pregnancy in Rats[1]

| Treatment | Dose (mg/kg/day) | Number of Rats Pregnant Number of Rats Treated | (Percent) | Fetal Viability Normal Fetuses/ Implantation Sites | (Percent) | Serum Progesterone ng/ml + S.E. | (Percent of Control) | Adrenal Wt. mg + SE |
|---|---|---|---|---|---|---|---|---|
| 3-(Acetyloxy)-17β-hydroxy-4,4,17-trimethyl-androsta-2,5-diene-2-carbonitrile | 16 | 0/6 | (0) | 0/60[a] | (0)[a] | 13.8 + 1.7[a] | (24)[a] | 56.8 + 2.0 |
|  | 8 | 0/7 | (0) | 0/81[a] | (0)[a] | 10.4 + 2.5[a] | (18)[a] | 62.0 + 2.5[a] |
|  | 4 | 1/8 | (13) | 6/82[a] | (7)[a] | 19.0 + 7.4[a] | (33)[a] | 60.0 + 4.2[a] |
| Control | — | 7/8 | (88) | 79/86 | (92) | 61.8 + 5.1[a] | (100) | 56.7 + 2.2 |
| Cyanoketone | 32 | 1/10 | (10) | 10/106[a] | (9)[a] | —[2] | —[2] | 60.3 + 1.6 |
|  | 16 | 1/9 | (11) | 8/108[a] | (7)[a] | — | — | 61.3 + 3.0 |
|  | 8 | 1/9 | (11) | 11/112[a] | (10)[a] | — | — | 59.0 +0 2.6 |
|  | 4 | 4/7 | (57) | 46/84 | (55) | — | — | 75.9 + 6.1 |
|  | 2 | 6/6 | (100) | 56/77 | (72) | — | 64.1 + 5.2 | 55.8 + 4.1 |
|  | 1 | 5/5 | (100) | 54/56 | (96) | — | — |  |
| Control | — | 7/7 | (100) | 68/75 | (91) | 47.2 + 6.9 | (100) | 58.8 + 2.4 |
|  | — | 6/6 | (100) | 47/50 | (94) | — | — | 68.7 + 3.3 |

[1]Compounds were administered intragastrically once daily on days 10 of pregnancy in a vehicle consisting of PEG-400, propylene glycol and 100 percent ethanol (50:40:10, v:v:v). Serum for progesterone determination was drawn on day 11 of pregnancy, 24 hours after the initial injection of compound. The animals were autopsied on day 14 of pregnancy.
[2]— Not determined; presumed equivalent to day 11 values in Table 1.
[a]p < .01; [b]< .05 versus appropriate control.

What I claim is:
1. A method for the induction of menses or the termination of pregnancy which comprises administering an amount of a compound of the formula:

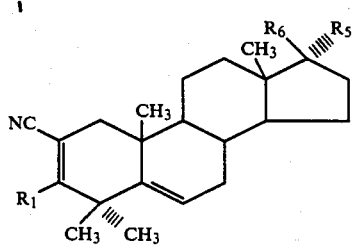

wherein $R_1$ is:
(a) hydroxy;
(b) $R_2COO-$;
(c) $HOOC-R_3-COO-$; or
(d) $R_4C(=O)-R_3-COO-$;
wherein $R_2$ is:
(a) alkyl of from 1 to 10 carbon atoms inclusive;
(b) oxacyloalkyl group containing from 4 to 7 carbon atoms and one ring oxygen atom; or
(c) cycloalkyl of from 5 to 10 carbon atoms, inclusive,
(d) ring-unsaturated oxacycloalkyl of from 4 to 7 carbon atoms and one ring oxygen atom; or
(e) ring-unsaturated cycloalkyl of from 5 to 10 carbon atoms, inclusive;
wherein $R_3$ is:
(a) alkylene of from 1 to 10 carbon atoms, inclusive;
(b) cycloalkylene of from 5 to 10 carbon atoms, inclusive;
wherein $R_4$ is:
(a) alkyl of from 1 to 6 carbon atoms, inclusive;

wherein $R_5$ is:
  (a) hydrogen; or
  (b) alkyl of from 1 to 6 carbon atoms, inclusive;
wherein $R_6$ is:
  (a) hydroxy.

2. A method according to claim 1 using 3-(acetyloxy)-17β-hydroxy-4,4,17α-trimethylandrosta-2,5-diene-2-carbonitrile.

3. A method according to claim 1 using 2-cyano-4,4,17α-trimethylandrosta-2,5-diene-3,17β-diacetate.

4. A method according to claim 1 using 3-(trimethylacetyloxy)-17β-hydroxy-4,4,17α-trimethylandrosta-2,5-diene-2-carbonitrile.

5. A method according to claim 1 using 3-[3-(methoxycarbonyl)propanoyloxy]-17β-hydroxy-4,4,17α-trimethylandrosta-2,5-diene-2-carbonitrile.

6. A method according to claim 1 using 3-(2-furoyloxy)-17β-hydroxy-4,4,17α-trimethylandrosta-2,5-diene-2-carbonitrile.

* * * * *